US012802803B2

(12) United States Patent
Huang et al.

(10) Patent No.: US 12,802,803 B2
(45) Date of Patent: Nov. 17, 2026

(54) SYSTEMS AND METHODS FOR SMART INTERPOLATION OF ANNOTATIONS ON TOMOGRAPHIC IMAGES

(71) Applicants: Gaofeng Huang, Arlington, VA (US); Xue Feng, Ashburn, VA (US); Kanchan Ghimire, Herndon, VA (US); Quan Chen, Lexington, KY (US)

(72) Inventors: Gaofeng Huang, Arlington, VA (US); Xue Feng, Ashburn, VA (US); Kanchan Ghimire, Herndon, VA (US); Quan Chen, Lexington, KY (US)

( * ) Notice: Subject to any disclaimer, the term of this patent is extended or adjusted under 35 U.S.C. 154(b) by 350 days.

(21) Appl. No.: 18/215,153

(22) Filed: Jun. 27, 2023

(65) Prior Publication Data

US 2025/0006344 A1 Jan. 2, 2025

(51) Int. Cl.
*G16H 30/40* (2018.01)
*G06T 7/00* (2017.01)

(52) U.S. Cl.
CPC ........... *G16H 30/40* (2018.01); *G06T 7/0012* (2013.01); *G06T 2207/10072* (2013.01); *G06T 2207/10081* (2013.01); *G06T 2207/10104* (2013.01); *G06T 2207/20104* (2013.01); *G06T 2207/30016* (2013.01); *G06T 2207/30096* (2013.01)

(58) Field of Classification Search
CPC .................. G16H 30/40; G06T 7/0012; G06T 2207/10072; G06T 2207/10081; G06T 2207/10104; G06T 2207/20104; G06T 2207/30016; G06T 2207/30096
See application file for complete search history.

(56) References Cited

U.S. PATENT DOCUMENTS

2012/0087561 A1* 4/2012 Guetter .................. G06T 7/174 382/131
2013/0033419 A1* 2/2013 Dror ......................... G06T 7/12 382/128
2016/0093110 A1* 3/2016 Waschbusch ........... G06T 19/00 382/131
2017/0301085 A1* 10/2017 Riklin Raviv ......... G16H 40/63
2018/0182103 A1* 6/2018 Syeda-Mahmood ..... G06T 7/32
2020/0272841 A1* 8/2020 Han ..................... A61B 5/1073
2022/0012887 A1* 1/2022 Praceus ..................... G06T 7/11
2022/0199231 A1* 6/2022 Kim ....................... G16H 30/40
2023/0032702 A1* 2/2023 Alvarez-Valle ........... G06T 7/11
2023/0196698 A1* 6/2023 Gogin ..................... G06T 19/00 345/419
2024/0212159 A1* 6/2024 Katzmann ............. G16H 30/40

* cited by examiner

*Primary Examiner* — Jennifer Mehmood
*Assistant Examiner* — Jose M Torres

(57) ABSTRACT

The present disclosure relates to a method and apparatus for smart interpolation of annotations on tomographic images. The method includes receiving 3D images obtained by a CT, MRI or PET system, receiving labels with contours of regions-of-interest (ROIs) if labels are available for the received 3D images from an automatic segmentation algorithm or manual segmentation, creating empty labels if labels are not available, recording user changes on 2D slices of the labels, finding two neighboring 2D slices that the user has edited, running interpolation on the user changes, applying the interpolated changes to 2D slices not edited by the user, and performing post-processing to output final 3D segmentation of the ROIs.

15 Claims, 6 Drawing Sheets

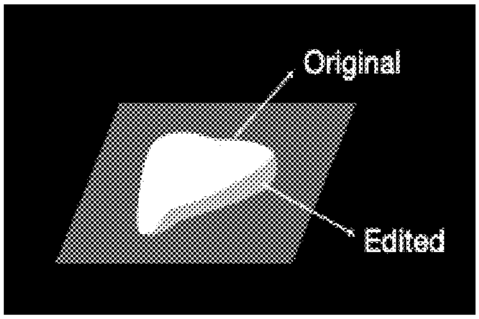
FIG. 3A
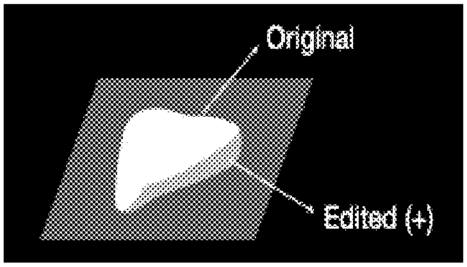
FIG. 3B
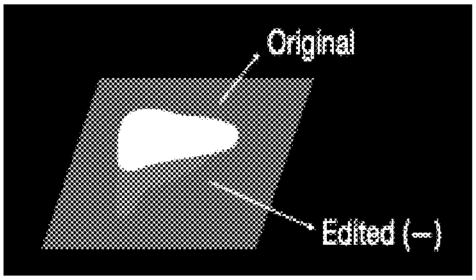
FIG. 3C
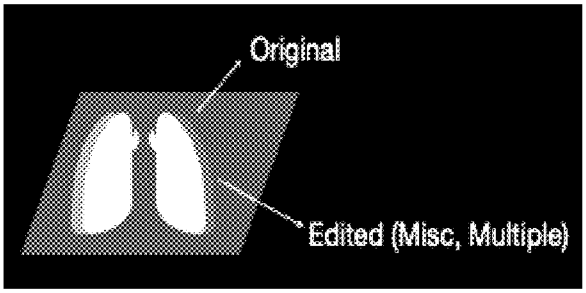
FIG. 3D
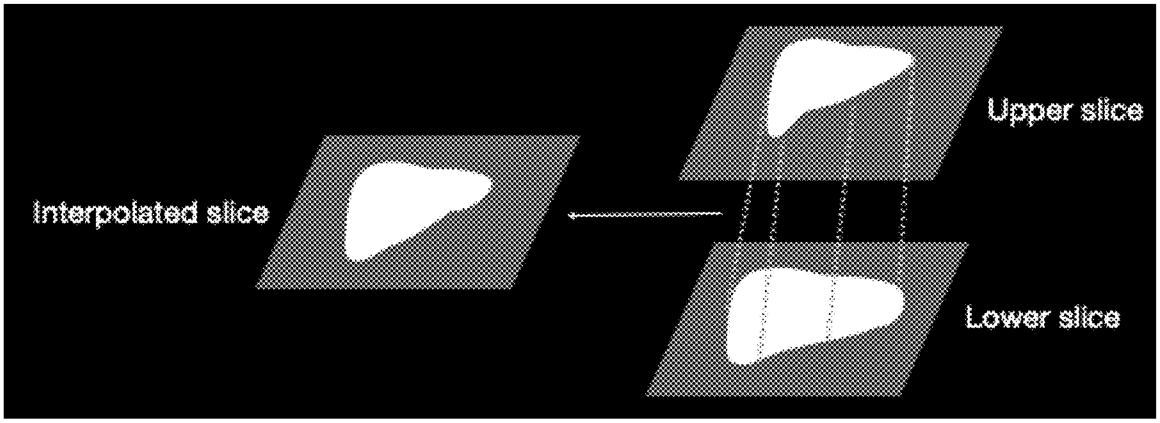
FIG. 3E
FIG. 3

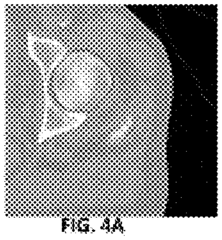
FIG. 4A
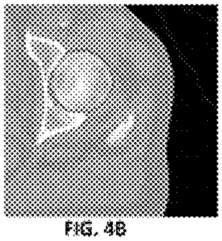
FIG. 4B
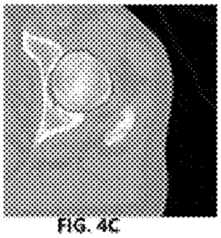
FIG. 4C
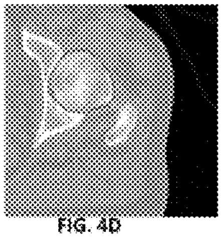
FIG. 4D
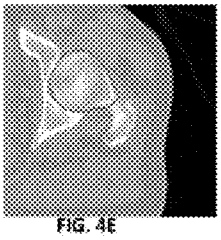
FIG. 4E
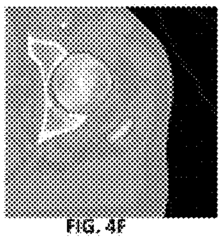
FIG. 4F
FIG. 4G
FIG. 4H
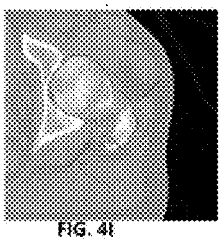
FIG. 4I
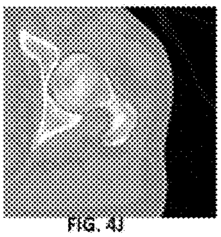
FIG. 4J
FIG. 4K
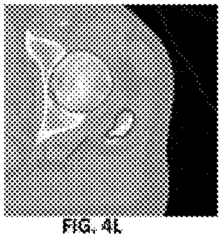
FIG. 4L
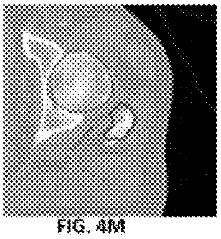
FIG. 4M
FIG. 4N
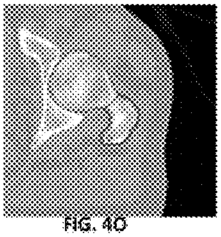
FIG. 4O
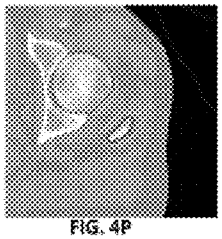
FIG. 4P
FIG. 4Q
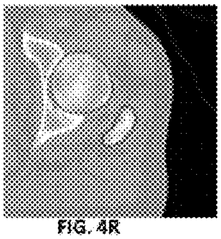
FIG. 4R
FIG. 4S
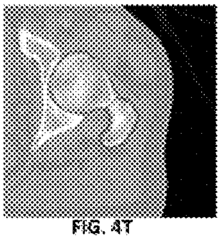
FIG. 4T
FIG. 4

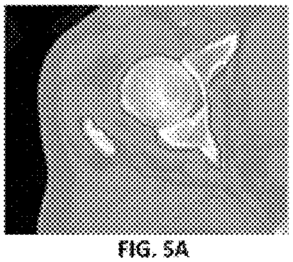
FIG. 5A
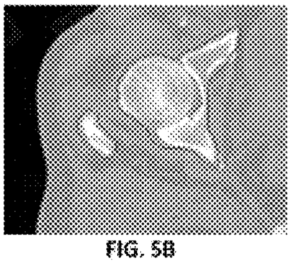
FIG. 5B
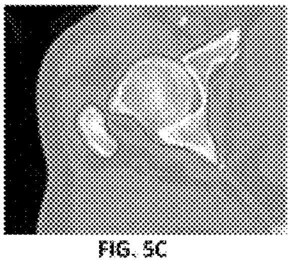
FIG. 5C
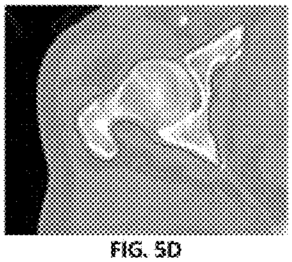
FIG. 5D
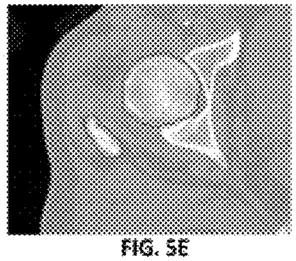
FIG. 5E
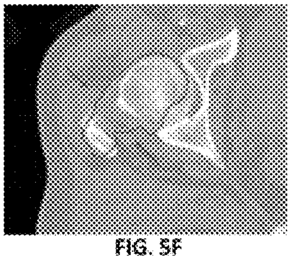
FIG. 5F
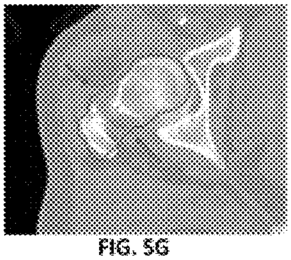
FIG. 5G
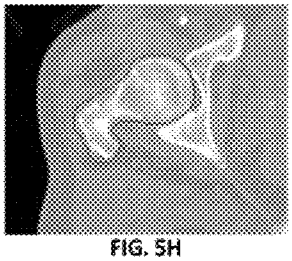
FIG. 5H
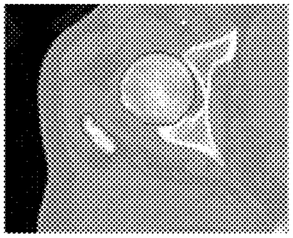
FIG. 5I
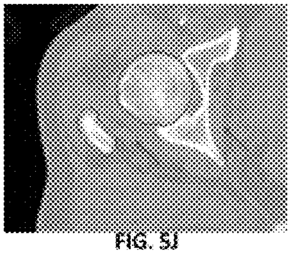
FIG. 5J
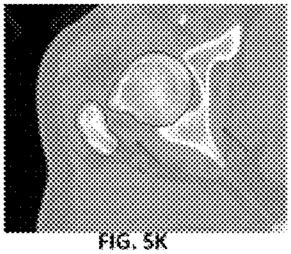
FIG. 5K
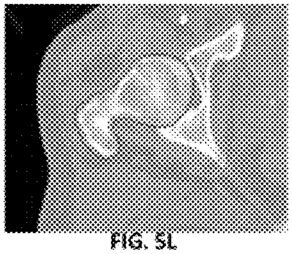
FIG. 5L
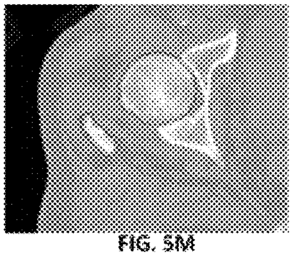
FIG. 5M
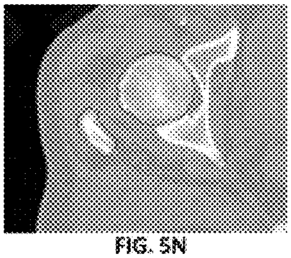
FIG. 5N
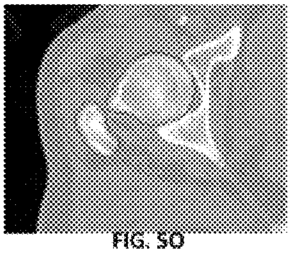
FIG. 5O
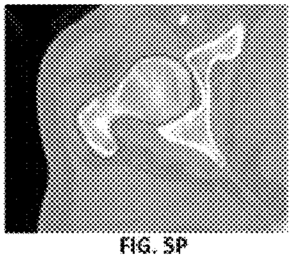
FIG. 5P
FIG. 5

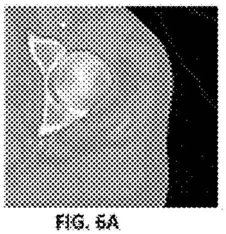
FIG. 6A
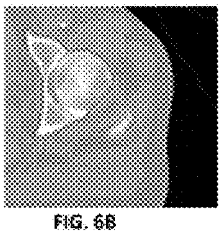
FIG. 6B
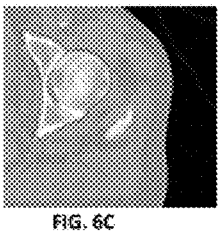
FIG. 6C
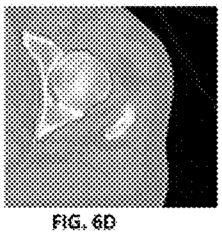
FIG. 6D
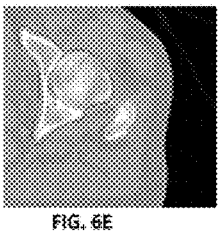
FIG. 6E
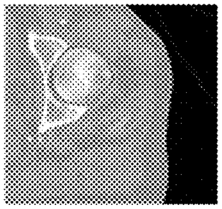
FIG. 6F
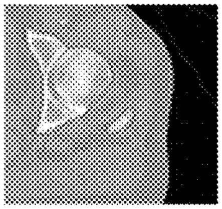
FIG. 6G
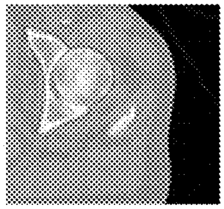
FIG. 6H
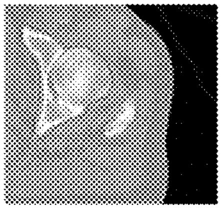
FIG. 6I
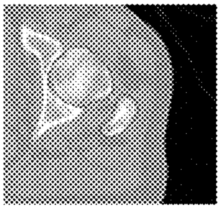
FIG. 6J
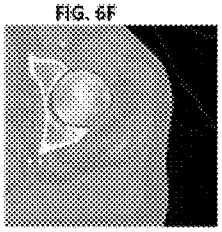
FIG. 6K
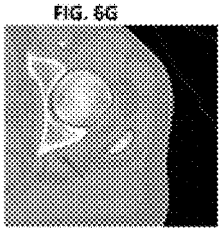
FIG. 6L
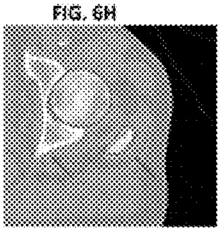
FIG. 6M
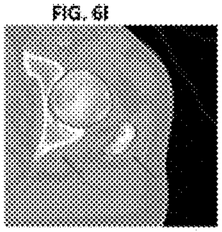
FIG. 6N
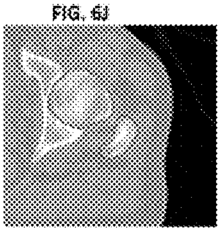
FIG. 6O
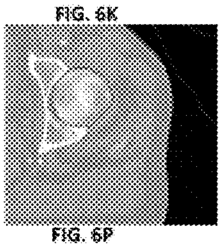
FIG. 6P
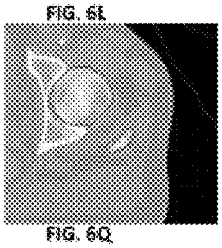
FIG. 6Q
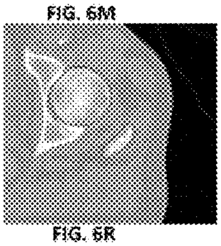
FIG. 6R
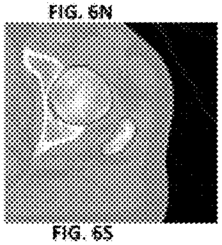
FIG. 6S
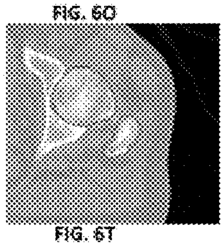
FIG. 6T
FIG. 6

SYSTEMS AND METHODS FOR SMART INTERPOLATION OF ANNOTATIONS ON TOMOGRAPHIC IMAGES

STATEMENT OF GOVERNMENT INTEREST

This invention was made with government support under Grant No. R44CA254844 awarded by The National Institute of Health. The government has certain rights in the invention.

CROSS-REFERENCE TO RELATED APPLICATION

Not applicable.

FIELD

This disclosure relates to operations on tomographic images, such as computed tomography (CT), magnetic resonance imaging (MRI) and positron emission tomography (PET), that develop and validate a framework for smart interpolation of annotations on tomographic images.

BACKGROUND

In current clinical practice, manual annotation is the most widely used method of segmentation of organs, tumors or other anatomical features. It is often a tedious and time-consuming task as radiologists spend significant time meticulously delineating or manually tracing the boundaries of regions-of-interest (ROIs) on imaging data. During the manual delineation process, the expert annotators have to go through the entire tomographic images slice-by-slice. While a simple solution to this problem is to implement an automated algorithm, the automated algorithm may not delineate ROIs well enough to be used in clinical practice. Oftentimes, the manual annotators need to review and verify the automatically annotated regions and the editing process has similar problems of the task being tedious and time consuming. The editing is an essential step even for manual annotation processes where multiple annotators are often involved in clinical practice. Therefore, a less tedious and burdensome approach is needed to perform or edit annotations manually.

To assist the manual annotation process, there are a number of interpolation software that allow annotators to contour on some 2D slices and then the software interpolates the contours to the skipped slices. This minimizes the burden of performing annotation on all slices, thereby saving manual time and effort. However, these existing software have adopted an approach of only utilizing the information of newly drawn contours (and not of existing contours) and is only suitable for performing annotations as opposed to editing the existing contours. For instance, if a contour/ROI needs editing on slices 100-120, editing needs to be performed on all those slices since interpolation may not be available on skipped slices since old contour already exists on those skipped slices. In some cases, interpolation may be available on skipped slices but since the interpolation is based on the entire contour, interpolation may be inaccurate since it doesn't take into account the actual changes made to the contour. Smart interpolation (our method), on the other hand, focuses on changes in the 2D slices from the previous iteration/existing contour. As such, changes on the edited slices are first tracked during editing, then the interpolation is performed on those changes and finally the interpolated changes are applied to the original contours to create edited contours on the skipped slices. The changes on the contours supported by our method include addition, subtraction or a combination of both. Our algorithm accepts the initial/existing contour from both automatic segmentation method or manual segmentation. In cases where initial contour is not present, it allows manual annotators to draw the necessary contours. Furthermore, our method allows the annotators to perform editing in an iterative fashion where initial editing might not be sufficient or when multiple annotators are involved in the editing process.

Therefore, smart interpolation provides a simple, fast, and robust 3D interpolation algorithm to help radiologists or other trained annotators in delineating and/or editing contours. It provides a solution that minimizes the need for delineated/edited slices and automates the completion of remaining slices based on the changes made to the contours. The interpolated contours maintain satisfactory quality even when skipping 3 to 5 slices, resulting in reducing at least 70 percent of the annotation time on average, without compromising the segmentation quality.

SUMMARY

Examples of the present disclosure provide a method for smart interpolation of annotations on tomographic images using an image processing-based approach to assist annotators for fast and reliable delineation of regions-of-interest (ROIs).

According to the first aspect of the present disclosure, a computer-implemented method for the smart interpolation of annotations. The methods may include: receiving 3D images obtained by a CT, MRI or PET system, partitioning the received 3D images along a specified axis to generate a plurality of 2D slices, receiving 3D segmentation labels of regions-of-interest (ROIs) if 3D segmentation labels are available for the received 3D images either from automatic segmentation algorithm or manual segmentation, creating empty 3D segmentation labels if 3D segmentation labels are not available, recording user changes on each of the plurality of 2D slices, converting user changes to the added labels and subtracted labels on each of the plurality of 2D slices, finding two neighboring 2D slices from the plurality of 2D slices that the user has changed, running interpolation on the added and subtracted labels of the two neighboring 2D slices respectively to generate interpolated added and subtracted labels, applying the interpolated added and subtracted labels to existing labels on each 2D slice not changed by the user, and performing post-processing to output the final 3D segmentation labels of the same ROIs.

According to a second aspect of the present disclosure, an apparatus for the smart interpolation of annotations. The apparatus may include one or more processors, a display, and a non-transitory computer-readable memory storing instructions executable by one or more processors. Wherein the instructions comprising receiving 3D images obtained by a CT, MRI or PET system, partitioning the received 3D images along a specified axis to generate a plurality of 2D slices, receiving 3D segmentation labels of regions-of-interest (ROIs) if 3D segmentation labels are available for the received 3D images either from automatic segmentation algorithm or manual segmentation, creating empty 3D segmentation labels if 3D segmentation labels are not available, recording user changes on each of the plurality of 2D slices, converting user changes to the added labels and subtracted labels on each of the plurality of 2D slices, finding two neighboring 2D slices from the plurality of 2D slices that the user has changed, running interpolation on the added and subtracted labels of the two neighboring 2D slices respectively to generate interpolated added and subtracted labels, applying the interpolated added and subtracted labels to existing labels on each 2D slice not changed by the user, and performing post-processing to output the final 3D segmentation labels of the same ROIs.

According to a third aspect of an example of the present disclosure, a non-transitory computer-readable storage medium having stored therein instructions is provided. When the instructions are executed by one or more processors or one or more graphic processing units (GPUs) of the apparatus, the instructions cause the apparatus to receive 3D images obtained by a CT, MRI or PET system, partition the received 3D images along a specified axis to generate a plurality of 2D slices, receive 3D segmentation labels of regions-of-interest (ROIs) if 3D segmentation labels are available for the received 3D images either from automatic segmentation algorithm or manual segmentation, create empty 3D segmentation labels if 3D segmentation labels are not available, record user changes on each of the plurality of 2D slices, convert user changes to the added labels and subtracted labels on each of the plurality of 2D slices, find two neighboring 2D slices from the plurality of 2D slices that the user has changed, run interpolation on the added and subtracted labels of the two neighboring 2D slices respectively to generate interpolated added and subtracted labels, apply the interpolated added and subtracted labels to existing labels on each 2D slice not changed by the user, and perform post-processing to output the final 3D segmentation labels of the same ROIs.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 3 is a method diagram showing the implementation of smart interpolation algorithm, according to an example of the present disclosure.

FIG. 3A is an example of a structure's contour after editing, with the yellow region showing the edited portion.

FIG. 3B is an example of a structure's contour after editing, with the yellow region showing the edited portion as a positive changed area.

FIG. 3C is an example of a structure's contour after editing, with the blue region showing the edited portion as a negative changed area.

FIG. 3D is an example of a structure's contour after editing, with the yellow region showing the edited portion as a positive changed area and the blue region showing the edited portion as a negative changed area. The changed area is regarded as miscellaneous (misc.) since it includes both the positive and negative changed area.

FIG. 3E shows the implementation of 3D interpolation, with an example of an interpolated slice between two changed slices (upper and lower).

FIG. 4 shows an example of editing performed on an under-annotated region-of-interest (ROI) and comparison of interpolation based on changed area (smart interpolation) vs interpolation based on the entire edited contours (other) against the ground-truth. The orange arrows denote edited areas and the red arrows denote interpolated areas.

FIG. 4A shows a 2D slice 231 with under-annotation of an ROI that needs editing, with dice score of 0.9506 calculated against the ground-truth.

FIG. 4B shows a 2D slice 232 with under-annotation of an ROI that needs editing, with dice score of 0.9211 calculated against the ground-truth.

FIG. 4C shows a 2D slice 233 with under-annotation of an ROI that needs editing, with dice score of 0.8925 calculated against the ground-truth.

FIG. 4D shows a 2D slice 234 with under-annotation of an ROI that needs editing, with dice score of 0.8711 calculated against the ground-truth.

FIG. 4E shows a 2D slice 235 with under-annotation of an ROI that needs editing, with dice score of 0.8381 calculated against the ground-truth.

FIG. 4F shows a 2D slice 231 after manual editing performed on the 2D slice of FIG. 4A, with a dice score of 0.993 calculated against the ground-truth.

FIG. 4G shows a 2D slice 232 after interpolation based on the entire edited contour that created unnecessary interpolation/over-segmentation, with a dice score of 0.8539 calculated against the ground-truth.

FIG. 4H shows a 2D slice 233 after interpolation based on the entire edited contour that created unnecessary interpolation/over-segmentation, with a dice score of 0.8465 calculated against the ground-truth.

FIG. 4I shows a 2D slice 234 after interpolation based on the entire edited contour that created unnecessary interpolation/over-segmentation, with a dice score of 0.8715 calculated against the ground-truth.

FIG. 4J shows a 2D slice 235 after manual editing performed on the slice of FIG. 4E, with a dice score of 0.9883 calculated against the ground-truth.

FIG. 4K shows a 2D slice 231 after manual editing performed on the 2D slice of FIG. 4A, with a dice score of 0.993 calculated against the ground-truth.

FIG. 4L shows a 2D slice 232 after interpolation based on the changed area (smart interpolation), with a dice score of 0.9698 calculated against the ground-truth.

FIG. 4M shows a 2D slice 233 after interpolation based on the changed area (smart interpolation), with a dice score of 0.968 calculated against the ground-truth.

FIG. 4N shows a 2D slice 234 after interpolation based on the changed area (smart interpolation), with a dice score of 0.9694 calculated against the ground-truth.

FIG. 4O shows a 2D slice 235 after manual editing performed on the slice of FIG. 4E, with a dice score of 0.9883 calculated against the ground-truth.

FIG. 4P shows a 2D slice 231 with ground-truth.

FIG. 4Q shows a 2D slice 232 with ground-truth.

FIG. 4R shows a 2D slice 233 with ground-truth.

FIG. 4S shows a 2D slice 234 with ground-truth.

FIG. 4T shows a 2D slice 235 with ground-truth.

FIG. 5 shows an example of editing performed on an over-annotated region-of-interest (ROI) and comparison of interpolation based on changed area (smart interpolation) vs interpolation based on the entire edited contours (other)

Figure 1:
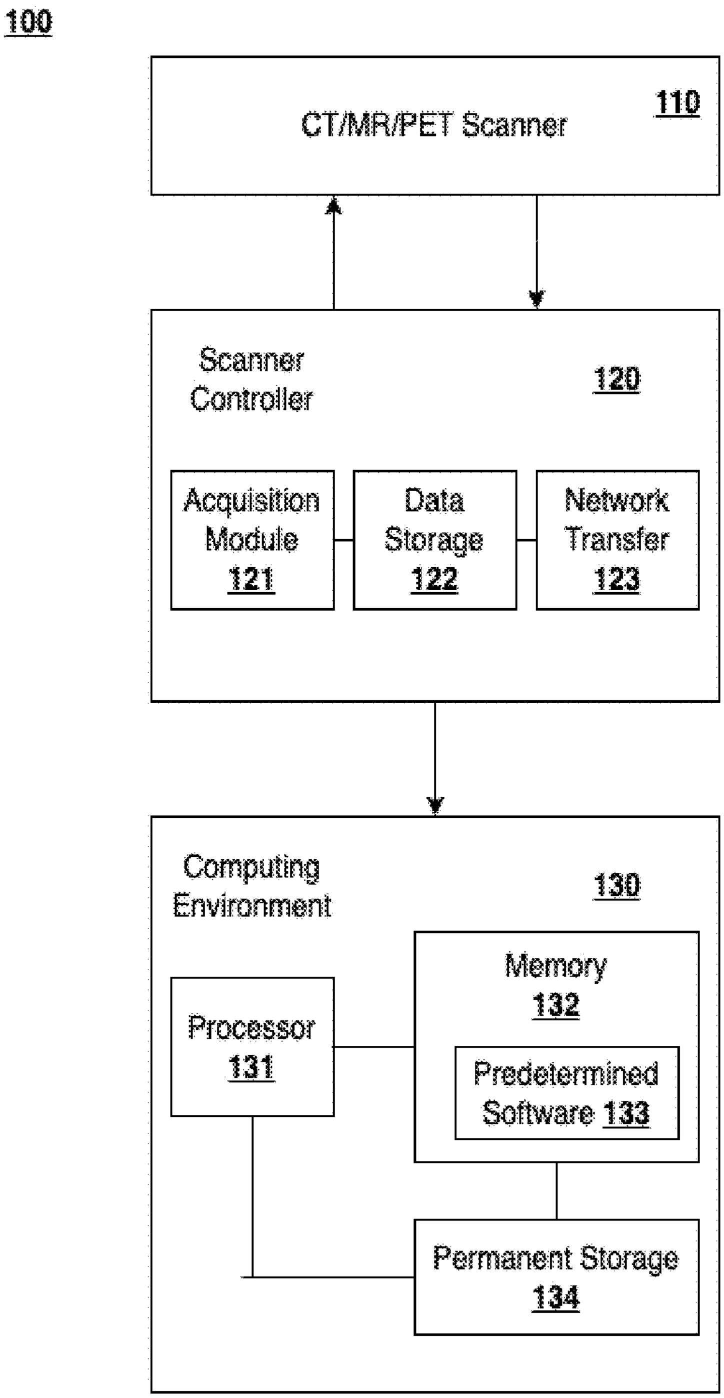
FIG. 1 is a system diagram of CT/MRI/PET scanner, controller and computing environment illustrating an operating environment capable of implementing aspects of the present disclosure.

against the ground-truth. The orange arrows denote edited areas and the red arrows denote interpolated areas.

FIG. 5A shows a 2D slice 235 with over-annotation of an ROI that needs editing, with dice score of 0.7065 calculated against the ground-truth.

FIG. 5B shows a 2D slice 236 with over-annotation of an ROI that needs editing, with dice score of 0.7112 calculated against the ground-truth.

FIG. 5C shows a 2D slice 237 with over-annotation of an ROI that needs editing, with dice score of 0.7325 calculated against the ground-truth.

FIG. 5D shows a 2D slice 238 with over-annotation of an ROI that needs editing, with dice score of 0.7311 calculated against the ground-truth.

FIG. 5E shows a 2D slice 235 after manual editing performed on the slice of FIG. 5A, with a dice score of 0.9677 calculated against the ground-truth.

FIG. 5F shows a 2D slice 236 after interpolation based on the entire edited contour that created unnecessary interpolation/over-segmentation, with a dice score of 0.7826 calculated against the ground-truth.

FIG. 5G shows a 2D slice 237 after interpolation based on the entire edited contour that created unnecessary interpolation/over-segmentation, with a dice score of 0.8344 calculated against the ground-truth.

FIG. 5H shows a 2D slice 238 after manual editing performed on the slice of FIG. 5D, with a dice score of 0.965 calculated against the ground-truth.

FIG. 5I shows a 2D slice 235 after manual editing performed on the slice of FIG. 5A, with a dice score of 0.9882 calculated against the ground-truth.

FIG. 5J shows a 2D slice 236 after interpolation based on the changed area (smart interpolation), with a dice score of 0.986 calculated against the ground-truth.

FIG. 5K shows a 2D slice 237 after interpolation based on the changed area (smart interpolation), with a dice score of 0.9845 calculated against the ground-truth.

FIG. 5L shows a 2D slice 238 after manual editing performed on the 2D slice of FIG. 5D, with a dice score of 0.9818 calculated against the ground-truth.

FIG. 5M shows a 2D slice 235 with ground-truth.

FIG. 5N shows a 2D slice 236 with ground-truth.

FIG. 5O shows a 2D slice 237 with ground-truth.

FIG. 5P shows a 2D slice 238 with ground-truth.

FIG. 6 shows an example of editing performed on a region-of-interest (ROI) with a scenario of both under- and over-annotation and interpolation based on changed area (smart interpolation) against the ground-truth. The orange arrows denote edited areas and the red arrows denote interpolated areas.

FIG. 6A shows a 2D slice 230 with a scenario of both under- and over-annotation of an ROI that needs editing, with dice score of 0.6732 calculated against the ground-truth.

FIG. 6B shows a 2D slice 231 with a scenario of both under- and over-annotation of an ROI that needs editing, with dice score of 0.6508 calculated against the ground-truth.

FIG. 6C shows a 2D slice 232 with a scenario of both under- and over-annotation of an ROI that needs editing, with dice score of 0.6384 calculated against the ground-truth.

FIG. 6D shows a 2D slice 233 with a scenario of both under- and over-annotation of an ROI that needs editing, with dice score of 0.6211 calculated against the ground-truth.

FIG. 6E shows a 2D slice 234 with a scenario of both under- and over-annotation of an ROI that needs editing, with dice score of 0.609 calculated against the ground-truth.

FIG. 6F shows a 2D slice 230 after manual editing performed on the slice of FIG. 6A to fix the issue of over-annotation, with a dice score of 0.9905 calculated against the ground-truth.

FIG. 6G shows a 2D slice 231 after manual editing performed on the slice of FIG. 6B to fix the issue of under-annotation, with a dice score of 0.6896 calculated against the ground-truth.

FIG. 6H shows a 2D slice 232 with no manual editing on FIG. 6C, with a dice score of 0.6384 calculated against the ground-truth.

FIG. 6I shows a 2D slice 233 with no manual editing on FIG. 6D, with a dice score of 0.6211 calculated against the ground-truth.

FIG. 6J shows a 2D slice 234 after manual editing performed on the slice of FIG. 6E to fix the issue of both under- and over-annotation, with a dice score of 0.9793 calculated against the ground-truth.

FIG. 6K shows the same 2D slice 230 as FIG. 6F.

FIG. 6L shows a 2D slice 231 after manual editing performed on the slice of FIG. 6B to fix the issue of over-annotation, with a dice score of 0.9811 calculated against the ground-truth.

FIG. 6M shows a 2D slice 232 after interpolation based on the changed area (smart interpolation), with a dice score of 0.9707 calculated against the ground-truth.

FIG. 6N shows a 2D slice 233 after interpolation based on the changed area (smart interpolation), with a dice score of 0.9756 calculated against the ground-truth.

FIG. 6O shows a 2D slice 234 after manual editing performed on the slice of FIG. 6E, with a dice score of 0.9793 calculated against the ground-truth.

FIG. 6P shows a 2D slice 230 with ground-truth.

FIG. 6Q shows a 2D slice 231 with ground-truth.

FIG. 6R shows a 2D slice 232 with ground-truth.

FIG. 6S shows a 2D slice 233 with ground-truth.

FIG. 6T shows a 2D slice 234 with ground-truth.

DETAILED DESCRIPTION

Reference will now be made in detail to example embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the disclosure. Instead, they are merely examples of apparatuses and methods consistent with aspects related to the disclosure as recited in the appended claims.

The terminology used in the present disclosure is for the purpose of describing particular embodiments only and is not intended to limit the present disclosure. As used in the present disclosure and the appended claims, the singular forms “a,” “an,” and “the” are intended to include the plural forms as well, unless the context clearly indicates otherwise. It shall also be understood that the term “and/or” used herein is intended to signify and include any or all possible combinations of one or more of the associated listed items.

It shall be understood that, although the terms “first,” “second,” “third,” etc. may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to a judgment" depending on the context.

FIG. 1 shows a system diagram 100 of CT/MRI/PET scanner 110, controller 120, and computing environment 130. The CT/MRI/PET scanner 110 is used to obtain CT or MRI or PET images of a subject and is controlled by the scanner controller 120. The scanner controller 120 contains the acquisition module 121 that drives the CT/MRI/PET scanner 110, the data storage module 122 that stores the CT, MRI or PET images of different subjects, and the network transfer module 123 that sends the CT, MRI or PET images to another computing environment 130. The computing environment 130 contains processor 131, memory 132, and permanent storage 134 to perform given directions. In executing the directions, the predetermined software 133 is loaded into memory 132 and executed by processor 131 to yield the desired output.

The processing component 120 typically controls overall operations of the computing environment 130, such as the operations associated with display, data acquisition, data communications, and image processing. The processor 131 may include one or more processors to execute instructions to perform all or some of the steps in the above-described methods. Moreover, the processor 131 may include one or more modules which facilitate the interaction between the processor 131 and other components. The processor may be a Central Processing Unit (CPU), a microprocessor, a single chip machine, a GPU, or the like.

The memory 132 is configured to store various types of data to support the operation of the computing environment 130. Examples of such data comprise instructions for any applications or methods operated on the computing environment 130, CT, MRI or PET datasets, image data, etc. The memory 132 may be implemented by using any type of volatile or non-volatile memory devices, or a combination thereof, such as a static random-access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

In an embodiment, the computing environment 130 may be implemented with one or more application specific integrated circuits (ASICs), digital signal processors (DSPs), digital signal processing devices (DSPDs), programmable logic devices (PLDs), field programmable gate arrays (FPGAs), GPUs, controllers, micro-controllers, microprocessors, or other electronic components, for performing the above methods.

The method for smart interpolation of annotations on tomographic images is programmed as one set of predetermined software 133 and installed on the computing environment 130. When the computing environment 130 receives CT, MRI or PET images from scanner controller 120, the predetermined software 133 is executed to generate the annotations.

Figure 2:
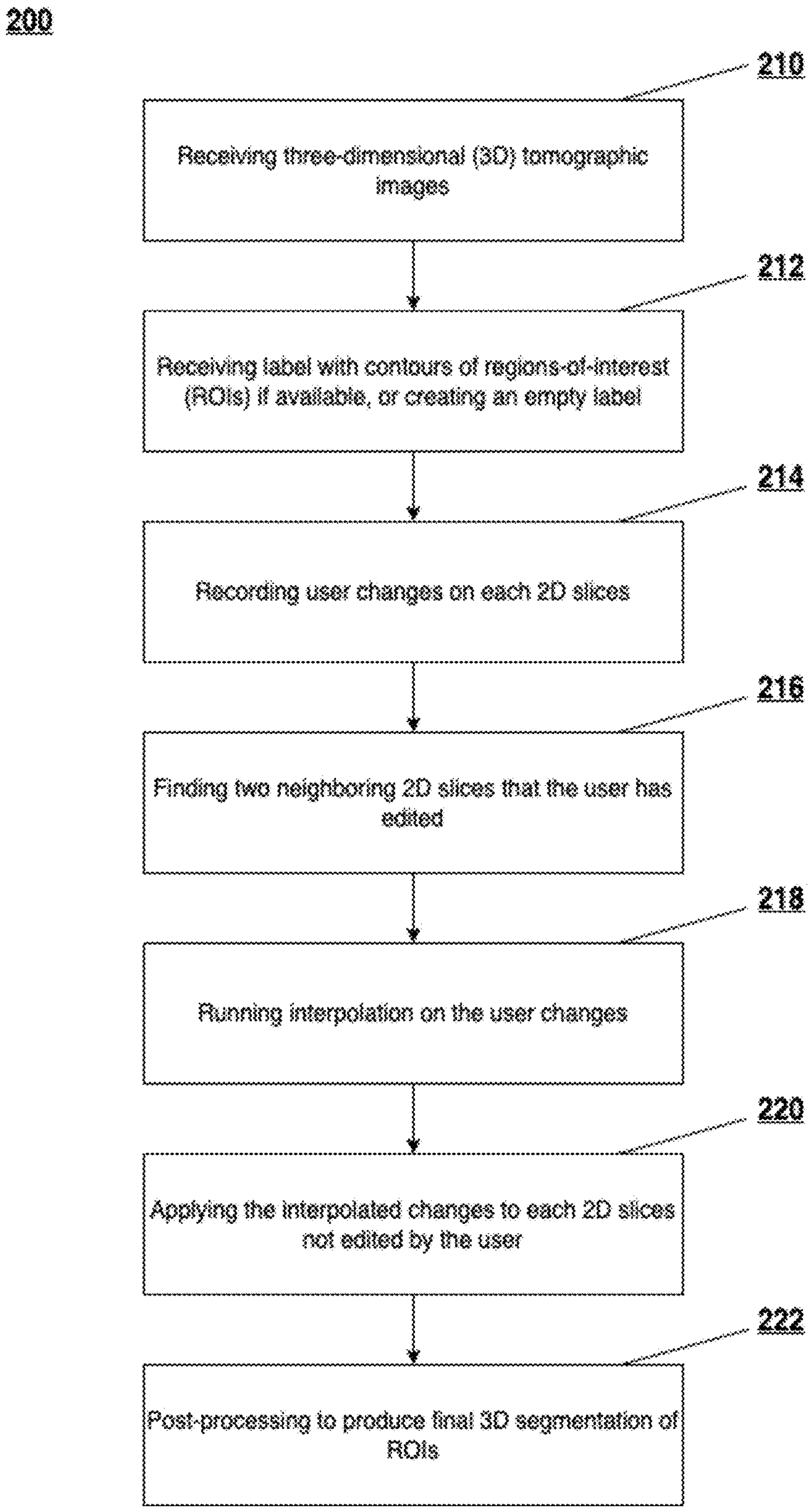
FIG. 2 is a flow chart illustrating a method for smart interpolation of annotations on tomographic images, according to an example of the present disclosure.

FIG. 2 shows an example flow chart setting forth the steps of a method 200 in accordance with the present disclosure.

In step 210, 3D tomographic images (CT, MRI or PET images) are received.

In step 212, corresponding label for 3D images with contours of regions-of-interest (ROIs) is received if the label is available from either automatic segmentation algorithm or manual delineation. If unavailable, empty 3D segmentation labels are created.

In step 214, user changes on each 2D slice are recorded. A history dictionary keeps track of the axis information and user changes made on each 2D slice. The user changes include addition, subtraction, or a combination of both addition and subtraction made to the segmentation labels of ROI. The changed area represents the difference between the changed ROI contour and the original ROI contour on a given 2D slice. FIG. 3A shows a contour with the user changed region shown in yellow.

In step 216, two neighboring changed 2D slices are found by looping through 2D slices recorded in the history dictionary from top to bottom. Once two neighboring changed 2D slices (upper and lower) are found, the algorithm checks to see if there are any slices between the upper and lower slices. All the steps described below will be skipped if there is no slice present between the upper and lower slices.

In step 218, polygon contours are first extracted from net changed areas and polygons are matched/paired between two neighboring changed 2D slices. For both the upper and lower slices, the difference between the edited ROI contour and original ROI contour is computed to extract the net changed area between the original and edited contour. Then polygon contours will be extracted from the net changed area on both the slices. The net changed area can be positive and negative. FIG. 3B shows an example of a positive edited area with a yellow region, whereas FIG. 3C shows an example of a negative edited area with a blue region. The positive polygons with less than 10 pixels are ignored. All remaining positive polygons will be dilated 5 pixels out but strictly within the union set of edited ROI label and original ROI label. The negative polygons with less than 10 pixels are ignored. All remaining negative polygons will be dilated 5 pixels out without touching the intersection set of edited ROI contour and original ROI contour. The morphological step is to avoid generating disconnected interpolated results. If there is no change in the ROI labels (i.e., no polygons) on both the slices, the steps described below will be skipped and the algorithm continues to search for the next two adjacent changed slices.

The positive or negative polygons are calculated respectively for the following steps. Assuming there are M polygons on the upper slice and N polygons on the lower slice, the next step is to match the polygons from the upper and lower slice to create pairs. First, the centroid for each of the polygons is computed by calculating the mean of all points in the polygon. Then the distance is calculated between centroids of each of the M polygons and each of the N polygons. Based on the shortest distance between the centroids, each of the M polygons is assigned a polygon from N polygons as the matched/paired polygon. Note that each of the M polygons is paired with only one closest polygon from the N polygons while each of the N polygons can be paired with zero or multiple polygons from the M polygons. Hence, there are M pairs of polygons.

For each pair of polygons, an iterative closest point (ICP) algorithm is used to register the polygons. First, a point from the upper slice is extracted. Then, using the ICP algorithm, the transformation (combination of rotation and translation) matrix is computed using distance minimization technique where distance is the sum of squared differences between the coordinates of the matched pair. Using the obtained transformation, the point from the upper slice is transformed. Then, the angle/slope of this point in the transformed point is computed with respect to the centroid of the given polygon. On the paired polygon of the upper slice found on the lower slice, a line is drawn from the centroid with the calculated angle/slope in the above step. The matched point on the lower slice is determined as the point that intersects the line with the polygon. After determining the matched point, the point is inserted into the original point on the lower slice.

Then, interpolation of changes is performed by first resampling a set of 5 additional corresponding points between the registered polygons from two adjacent edited slices. Then, the linearly interpolated polygon is calculated based on the resampled point pairs. FIG. 3E shows an example of an interpolated slice from two changed slices (upper and lower).

In step 220, the interpolated changes are applied to existing labels on each unchanged 2D slice.

Finally in step 222, post-processing is applied to produce final 3D segmentation labels of the same ROIs. For that, smoothing and filling holes is applied. The smoothing method is first binary dilation with 5 pixels, followed by binary erosion with 5 pixels. If there exist holes in the upper or lower slices (e.g. an index with 1 for existence and 0 for inexistence), the slices in between calculate the linearly interpolated decision to fill holes (with the index <0.5). For positive changes, the interpolated areas are assigned with 1 in the original slice. For negative changes, the interpolated areas are assigned with 0 in the original slice. Then the label after removing the interpolated negative areas will be measured to keep all large areas (area threshold is 1/10 of the largest area) because some small areas close to the boundary are always not removed.

To validate the smart interpolation algorithm, we performed some experiments. FIG. 4 is an example of a case with under-annotation of an ROI that needs to be edited. In this example, manual annotation/editing was performed on 2D slices, by skipping some slices to reduce the manual time and effort. More specifically, slices 231-235 is shown in the figure of which, slices 231 and 235 were manually edited by skipping n=3 (slices 232, 233, 234) slices in between. The performance metric used is the calculation of dice score with the ground-truth. To show the effectiveness of smart interpolation (interpolation based on the changed area after editing), comparison was made against another method where interpolation was based on the entire edited contours. FIG. 4G (Dice 0.8539) vs FIG. 4L (Dice 0.9698), FIG. 4H (Dice 0.8465) vs FIG. 4M (Dice 0.968), and FIG. 1 (0.8715) vs FIG. 4N (0.9649) demonstrated the superiority of the smart interpolation method compared against the other interpolation method. Furthermore, it also demonstrated that smart interpolation yields good performance while skipping slices, which results in reduced manual efforts and time without compromising the quality of the annotation.

Similarly, FIG. 5 is an example of a case with over-annotation of an ROI that needs to be edited. In this example, manual annotation/editing was performed on 2D slices, by skipping some slices to reduce the manual time and effort. More specifically, slices 235-238 is shown in the figure of which, slices 235 and 238 were manually edited by skipping n=2 (slices 236, 237) slices in between. The performance metric used is the calculation of dice score with the ground-truth. To show the effectiveness of smart interpolation (interpolation based on the changed area after editing), comparison was made against another method where interpolation was based on the entire edited contours. FIG. 5F (Dice 0.7826) vs FIG. 5J (Dice 0.986), and FIG. 5G (Dice 0.8344) vs FIG. 5K (Dice 0.9845) demonstrated the superiority of the smart interpolation method compared against the other interpolation method. Furthermore, it also demonstrated that smart interpolation yields good performance while skipping slices, which results in reduced manual efforts and time without compromising the quality of the annotation.

Furthermore, FIG. 6 shows that our smart interpolation algorithm is also applicable with both positive and negative changes at the same time. In a scenario where both under- and over-annotation needs to be fixed via editing, smart interpolation accounts for changed areas for both cases. FIG. 6C shows slice 232 that needs editing for both under- and over-annotation. In such a case, editing other slices (slices 230, 231 and 234) and running the smart interpolation algorithm improved the Dice score from 0.6384 (FIG. 6C) to Dice score of 0.970 (FIG. 6M).

Further experiments were performed to determine the ideal 'n' for skipping slices. On average, skipping about 10 slices while editing and running smart interpolation yield dice improvement of about 89% when compared to the contours in need of editing. Similarly, skipping about 5 slices while editing and running smart interpolation yields dice improvement of about 95%. Skipping about 3 to 5 slices while editing and running smart interpolation yields dice improvement of about 97%. Finally, skipping about 1 to 2 slices while editing and running smart interpolation also yields dice improvement of about 97%. Therefore, we have determined 'n' to be about 3-5 slices to yield the best performance while saving a significant amount of time.

What is claimed is:

1. A computer-implemented method for smart interpolation of annotations on tomographic images, the method comprising:

receive a 3D image obtained by a CT, MRI or PET system, the 3D image comprising a plurality of 2D slices;

receive 3D segmentation labels of regions-of-interest (ROIs), if 3D segmentation labels are available for the received 3D image either from an automatic segmentation algorithm or manual segmentation;

create empty 3D segmentation labels, if 3D segmentation labels are not available;

record user changes on each of the plurality of 2D slices, wherein recording the user changes comprises implementing a history dictionary to keep track of axis information identifying an axis of the 3D image and the user changes, and wherein the user changes include addition, subtraction, or a combination of addition and subtraction made to ROI contours;

find two neighboring 2D slices from the plurality of 2D slices that the user has changed, wherein finding the two neighboring 2D slices comprises looping through the history dictionary from top to bottom, a top neighboring changed 2D slice being an upper slice and a bottom neighboring changed 2D slice being a lower slice;

run interpolation on the user changes between the two neighboring 2D slices to generate interpolated changes;

apply the interpolated changes to each 2D slice not changed by the user; and perform post-processing to output final 3D segmentation labels of same the ROIs.

2. The computer-implemented method for smart interpolation of annotations on tomographic images according to claim 1, wherein running interpolation on the user changes comprises:

extracting polygon contours from changed areas on each of the two neighboring changed 2D slices;

pairing the polygon contours between the two neighboring changed 2D slices;

applying an iterative closest point algorithm to register the paired polygon contours; and linearly interpolating the extracted polygon contours between the two neighboring changed 2D slices.

3. The computer-implemented method for smart interpolation of annotations on tomographic images according to claim 2, wherein pairing the polygon contours between the two neighboring changed 2D slices comprises: computing centroids by calculating the mean of all the points in each of the polygons for both the neighboring changed 2D slices; and matching/pairing polygons between the neighboring changed 2D slices by calculating the shortest distance between the centroids.

4. The computer-implemented method for smart interpolation of annotations on tomographic images according to claim 2, wherein applying iterative closest point algorithm to register the paired polygon contours comprises: computing combination of rotation and translation for transformation matrix using distance minimization technique; transforming a point from the upper slice of the neighboring changed 2D slices using the obtained transformation matrix; determining matched point on the bottom slice of the neighboring changed 2D slices based on the calculated slope of the transformed point with respect to the centroid of the polygons; and registering the paired polygon contours by inserting the matched point into the original point on the lower slice of the neighboring changed 2D slices.

5. The computer-implemented method for smart interpolation of annotations on tomographic images according to claim 2, wherein linearly interpolating the extracted polygon contours between the two neighboring changed 2D slices comprises: resampling a set of 5 additional corresponding points between the registered polygons from the two neighboring changed 2D slices; and performing linear interpolation from the corresponding points to extract linearly interpolated polygon contours.

6. The computer-implemented method for smart interpolation of annotations on tomographic images according to claim 1, wherein applying the interpolated changes on each 2D slice not changed by the user comprises applying positive and negative portions of the interpolated changes to an existing contour on each 2D slice not changed by the user.

7. The computer-implemented method for smart interpolation of annotations on tomographic images according to claim 1, wherein performing post-processing to output final 3D segmentation labels of the ROIs comprises: performing binary dilation of 5 pixels followed by binary erosion of 5 pixels; filling holes; and removing regions having an area less than one-tenth of an area of the largest region.

8. An apparatus for smart interpolation of annotations on tomographic images, comprising:

one or more processors;

a display; and a non-transitory computer-readable memory storing instructions executable by the one or more processors, wherein the instructions, when executed by the one or more processors, cause the apparatus to:

receive a 3D image obtained by a CT, MRI or PET system, the 3D image comprising a plurality of 2D slices;

receive 3D segmentation labels of regions-of-interest (ROIs), if 3D segmentation labels are available for the received 3D image either from an automatic segmentation algorithm or manual segmentation;

create empty 3D segmentation labels, if 3D segmentation labels are not available;

record user changes on each of the plurality of 2D slices, wherein recording the user changes comprises implementing a history dictionary to keep track of axis information identifying an axis of the 3D image and the user changes, and wherein the user changes include addition, subtraction, or a combination of addition and subtraction made to ROI contours;

find two neighboring 2D slices from the plurality of 2D slices that the user has changed, wherein finding the two neighboring 2D slices comprises looping through the history dictionary from top to bottom, a top neighboring changed 2D slice being an upper slice and a bottom neighboring changed 2D slice being a lower slice;

run interpolation on the user changes between the two neighboring 2D slices to generate interpolated changes;

apply the interpolated changes to each 2D slice not changed by the user; and perform post-processing to output final 3D segmentation labels of the ROIs.

9. The apparatus for smart interpolation of annotations on tomographic images, according to claim 8, wherein the instructions further cause the apparatus to: extract polygon contours from changed areas on each of the two neighboring changed 2D slices; pair the polygon contours between the two neighboring changed 2D slices; apply an iterative closest point algorithm to register the paired polygon contours; and linearly interpolate the extracted polygon contours between the two neighboring changed 2D slices.

10. The apparatus for smart interpolation of annotations on tomographic images, according to claim 9, wherein the instructions further cause the apparatus to: compute centroids by calculating the mean of all the points in each of the polygons for both the neighboring changed 2D slices; and match/pair polygons between the neighboring changed 2D slices by calculating the shortest distance between the centroids.

11. The apparatus for smart interpolation of annotations on tomographic images, according to claim 9, wherein the instructions further cause the apparatus to: compute combination of rotation and translation for transformation matrix using distance minimization technique; transform a point from the upper slice of the neighboring changed 2D slices using the obtained transformation matrix; determine matched point on the bottom slice of the neighboring changed 2D slices based on the calculated slope of the transformed point with respect to the centroid of the polygons; and register the paired polygon contours by inserting the matched point into the original point on the lower slice of the neighboring changed 2D slices.

12. The apparatus for smart interpolation of annotations on tomographic images, according to claim 9, wherein the instructions further cause the apparatus to: resample a set of 5 additional corresponding points between the registered polygons from the two neighboring changed 2D slices; and perform linear interpolation from the corresponding points to extract linearly interpolated polygon contours.

13. The apparatus for smart interpolation of annotations on tomographic images, according to claim 8, wherein the instructions further cause the apparatus to apply positive and negative portions of the interpolated changes to an existing contour on each 2D slice not changed by the user.

14. The apparatus for smart interpolation of annotations on tomographic images, according to claim 8, wherein the instructions further cause the apparatus to: perform binary dilation of 5 pixels followed by binary erosion of 5 pixels; fill holes; and remove regions having an area less than one-tenth of an area of the largest region.

15. A non-transitory computer-readable storage medium having stored therein instructions that, when executed by one or more processors of an apparatus, cause the apparatus to perform acts comprising:

receive a 3D image obtained by a CT, MRI or PET system, the 3D image comprising a plurality of 2D slices;

receive 3D segmentation labels of regions-of-interest (ROIs), if 3D segmentation labels are available for the received 3D image either from an automatic segmentation algorithm or manual segmentation;

create empty 3D segmentation labels, if 3D segmentation labels are not available;

record user changes on each of the plurality of 2D slices, wherein recording the user changes comprises implementing a history dictionary to keep track of axis information identifying an axis of the 3D image and the user changes, and wherein the user changes include addition, subtraction, or a combination of addition and subtraction made to ROI contours;

find two neighboring 2D slices from the plurality of 2D slices that the user has changed, wherein finding the two neighboring 2D slices comprises looping through the history dictionary from top to bottom, a top neighboring changed 2D slice being an upper slice and a bottom neighboring changed 2D slice being a lower slice;

run interpolation on the user changes between the two neighboring 2D slices to generate interpolated changes;

apply the interpolated changes to each 2D slice not changed by the user; and perform post-processing to output final 3D segmentation labels of the ROIs.

* * * * *